(12) United States Patent
Fajt et al.

(10) Patent No.: US 10,513,910 B2
(45) Date of Patent: Dec. 24, 2019

(54) METHODS OF MICROBIAL MEASURING AND CONTROL

(71) Applicant: M-I L.L.C., Houston, TX (US)

(72) Inventors: James Fajt, College Station, TX (US); Abraham Zambrano, Cove, AK (US)

(73) Assignee: M-I L.L.C., Houston, TX (US)

(*) Notice: Subject to any disclaimer, the term of this patent is extended or adjusted under 35 U.S.C. 154(b) by 0 days.

(21) Appl. No.: 15/756,582

(22) PCT Filed: Mar. 3, 2016

(86) PCT No.: PCT/US2016/020672
§ 371 (c)(1),
(2) Date: Mar. 1, 2018

(87) PCT Pub. No.: WO2017/048320
PCT Pub. Date: Mar. 23, 2017

(65) Prior Publication Data
US 2018/0179858 A1    Jun. 28, 2018

Related U.S. Application Data

(60) Provisional application No. 62/218,344, filed on Sep. 14, 2015, provisional application No. 62/218,893, filed on Sep. 15, 2015.

(51) Int. Cl.
*C09K 8/04*       (2006.01)
*E21B 37/00*      (2006.01)
(Continued)

(52) U.S. Cl.
CPC .............. *E21B 37/00* (2013.01); *A01N 33/12* (2013.01); *A01N 35/02* (2013.01); *A01N 37/34* (2013.01);
(Continued)

(58) Field of Classification Search
CPC .............. C09K 8/04; C09K 8/66; E21B 37/00
(Continued)

(56) References Cited

U.S. PATENT DOCUMENTS 5,016,714 A * 5/1991 McCabe ................ C09K 8/605
166/308.1
2005/0034856 A1    2/2005 Lee et al.
(Continued)

FOREIGN PATENT DOCUMENTS

WO    2014/085333 A1    6/2014

OTHER PUBLICATIONS

International Search Report and Written Opinion for the equivalent International patent application PCT/US2016/020672 dated Jun. 16, 2016.
(Continued)

*Primary Examiner* — Zakiya W Bates
*Assistant Examiner* — Ashish K Varma

(57) ABSTRACT

The present disclosure relates to methods of controlling a microbial level in an aqueous fluid or a solid component used in an oilfield operation or a pre- or post-production process associated with wellbore production, the method comprising: measuring a microbial parameter of the aqueous fluid; and subsequently using the measured microbial parameter to decide on an appropriate antimicrobial treatment. These proposals also relate to methods further including monitoring of a microbial parameter in such a fluid or on such a solid component over a period of time. The methods and aspects of the present disclosure may be applied in any oilfield operation or a pre- or post-production process associated with wellbore production.

15 Claims, 6 Drawing Sheets

(51) Int. Cl.
*C09K 8/60* (2006.01)
*C09K 8/66* (2006.01)
*C09K 8/68* (2006.01)
*C09K 8/86* (2006.01)
*A01N 33/12* (2006.01)
*A01N 35/02* (2006.01)
*A01N 37/34* (2006.01)
*A01N 43/88* (2006.01)
*A01N 57/20* (2006.01)
*A01N 59/08* (2006.01)
*C09K 8/84* (2006.01)
*C12Q 1/06* (2006.01)
*E21B 47/00* (2012.01)
*E21B 43/26* (2006.01)

(52) U.S. Cl.
CPC ............ *A01N 43/88* (2013.01); *A01N 57/20* (2013.01); *A01N 59/08* (2013.01); *C09K 8/04* (2013.01); *C09K 8/605* (2013.01); *C09K 8/66* (2013.01); *C09K 8/68* (2013.01); *C09K 8/84* (2013.01); *C09K 8/86* (2013.01); *C12Q 1/06* (2013.01); *E21B 47/00* (2013.01); *E21B 43/26* (2013.01)

(58) Field of Classification Search
USPC ..................................... 166/305.1
See application file for complete search history.

(56) References Cited

U.S. PATENT DOCUMENTS

2012/0247763 A1  10/2012  Rakitsky et al.
2014/0090833 A1*  4/2014  Weaver .................. C09K 8/035
                                                166/246

OTHER PUBLICATIONS

International Preliminary Report on Patentability for the equivalent International patent application PCT/US2016/020672 dated Mar. 29, 2018.

* cited by examiner

METHODS OF MICROBIAL MEASURING AND CONTROL

RELATED APPLICATION

This application claims priority from U.S. Provisional Patent Application Ser. Nos. 62/218,344 and 62/218,893, which were filed on Sep. 14, 2015 and Sep. 15, 2015, the entire disclosure of which is incorporated herein by this reference.

TECHNICAL FIELD

The presently-disclosed subject matter relates to methods of measuring and control of a microbial population in an aqueous fluid used in, or for use in, an oilfield operation or a pre- or post-production process associated with wellbore production, or a microbial population on a solid component for use in such an aqueous fluid. These proposals also relate to methods further including monitoring of a microbial parameter in such a fluid or on such a solid component over a period of time.

BACKGROUND

Many oilfield operations include the use of a fluid being circulated through or otherwise introduced into the borehole. These fluids may include drilling fluids that are circulated during the drilling of the well, completion or production fluids that may be circulated during or after drilling during various completion operations, and fracturing ("fracking") fluids which may be used after drilling in order to stimulate the well to increase production from a hydrocarbon reservoir.

After a well is drilled into a subterranean geological formation that contains oil, natural gas, and water, efforts are made to maximize the production of the oil and/or gas. To increase the permeability and flow of the oil and/or gas to the surface, the drilled wells are often subjected to well stimulation. Well stimulation generally refers to several post drilling processes used to clean the well bore, enlarge channels, and increase pore space in the interval to be injected thus making it possible for fluids to move more readily into the formation.

A well stimulation process may generally include pumping engineered fluids at high pressure and rate into the subterranean geological formation. The fluid (usually water with some specialty high viscosity fluid additives) exceeds the rock strength and opens a fracture in the formation, which can extend out into the geological formation for as much as several hundred feet. Certain commonly used fracturing treatments generally comprise a carrier fluid (usually water or brine) and a polymer, which is also commonly referred to as a friction reducer. Many well stimulation fluids will further comprise a proppant. Other compositions used as fracturing fluids include water with additives, viscoelastic surfactant gels, gelled oils, crosslinkers, oxygen scavengers, and the like.

Aqueous fluids are also used at various other stages in the production of oil and/or natural gas. For example aqueous fluids may be used during any stage of drilling, production, fracturing, or completion of a wellbore. Similarly, aqueous fluids may be used during refining processes or as a component of treatment fluids for oilfield equipment such as pipes, lines, manifolds, or other conduits, tanks and storage vessels, and transport containers. Water may also be stored at an oilfield location, e.g. in a reservoir or pond, for use in oilfield processes (such as injection into a wellbore). This water may be stored above ground in a reservoir or pond or may be in a subterranean reservoir that can be accessed as necessary.

Water may be present in any of these processes, either alone or as a component of a wellbore or oilfield fluid. However, the water should be suitably free from undesirable microbes. If the water in these oilfield applications contains threshold levels of microbes, such as bacteria, fungus, etc., these can grow and proliferate on any surface with which the fluid is in contact or downhole. If left untreated, microbes and microbial biofilms (slimes) can cause deterioration of equipment, loss of efficiency in equipment, promotion and acceleration of corrosion on metal surfaces, or increased down time. For example, bacteria pose a risk to a well and production equipment because they can become attached to equipment and corrode metal, significantly weakening it or even to the point of failure. Bacteria can also grow and reproduce in the formation or oilfield apparatus and certain bacteria can produce $H_2S$ (hydrogen sulfide) resulting in a soured well. A soured well is can reduce the value of the asset by as much as 50%.

In addition to water used in oilfield fluids, a further source of microbes can be solid components incorporated into oilfield fluids. A common example may be proppant particles incorporated into wellbore stimulation fluids. These solids may have microbes deposited on their surface or incorporated in the solid particles. These microbes may then be released when the solids are incorporated into oilfield fluids and may inoculate the aqueous fluid with a microbial population.

Biocides and antimicrobials may be used to control microbial growth in the water. As used herein, "control" is defined to include both inhibition and removal.

Bacterial levels may be measured in oilfield fluids using a serial dilution method in which a sample is sequentially diluted tenfold in six progressive samples to give logarithmic dilutions 1×, 10×, 100×, 1,000×, 10,000×, 100,000×. These samples are placed under standard conditions conducive to bacterial growth and observations of bacterial growth are made over a period of time. The results may be provided in the industry in the form of a "log" number which represents the highest dilution in which bacterial growth was observed under the test conditions. The results from these standard tests can take days or even weeks to return.

The concept of measure, monitor, and control is an approach to the selection, application and post-application monitoring of oilfield operations, e.g. hydraulic fracking, production, etc. In order to tailor an antimicrobial treatment appropriately, monitoring of the microbial content of the water in the specific target process or fluid is advised to allow selection of appropriate microbial control parameters.

SUMMARY

This summary is provided to introduce a selection of concepts that are further described below. This summary is not intended to identify all key or essential features of the claimed subject matter, nor is it intended to be used to limit the scope of the claimed subject matter. To avoid unnecessary repetition, this summary does not list or suggest all possible combinations of features; features described with reference to one particular aspect of the invention may also be applicable to other aspects where appropriate and clearly compatible. Other aspects and advantages of the disclosure will be apparent form the description and claims considered as a whole.

The present proposals provide, a method of controlling a microbial level in an aqueous fluid used in, or for use in, an oilfield operation or a pre- or post-production process associated with wellbore production, the method comprising measuring a microbial parameter of the aqueous fluid; and subsequently using the measured microbial parameter to decide on an appropriate antimicrobial treatment. Optionally the method further includes performing the appropriate antimicrobial treatment.

The present proposals further include, a method of controlling a microbial level on a solid component for use in an aqueous fluid used in, or for use in, an oilfield operation or a pre- or post-production process associated with wellbore production, the method comprising measuring a microbial parameter of the solid component; and subsequently using the measured microbial parameter to decide on an appropriate antimicrobial treatment. Optionally the method further includes performing the appropriate antimicrobial treatment. In these methods, the appropriate antimicrobial treatment may be performed on the solid component prior to addition to the aqueous fluid; or may be performed on the aqueous fluid following addition of the solid component; or both prior to and following addition of the solid component to the aqueous fluid.

The present methods may further include monitoring of a microbial parameter in the aqueous fluid or on the solid component over a time period or at a second point in time after the initial measurement, and may further comprise adjusting the antimicrobial treatment according to changes in the microbial parameter over time.

The methods described herein may be applied in any area of oil or natural gas production from a wellbore, or in any post-production treatment of oil or natural gas obtained from a wellbore, e.g. refining. The methods may further be applied to any aqueous fluid aqueous fluid used in, or for use in, an oilfield operation or a pre- or post-production process associated with wellbore production.

In one aspect, the present proposals are generally directed to a method for preparing a wellbore fluid. Examples of the wellbore fluid may include water, chemicals, and a solid component (e.g. sand), or combinations thereof. The method may include determining a microbial parameter (e.g. the concentration of the microbial population) in a water stream by the methods described herein; selecting an appropriate antimicrobial treatment as discussed herein, and treating the water stream to reduce the microbial population. The chemicals and solid component (e.g. sand) may then be added to the treated water to produce a wellbore fluid. In some embodiments, the chemicals and/or solid component may provide an amount of a microbial population and/or interact with the microbial population in the water to produce an amount of the microbial population greater than originally determined for the water alone. Therefore, after the water interacts with the chemicals and/or solid component, the concentration of the microbial population in the wellbore fluid may be determined by the methods described herein and the wellbore fluid may be treated (as described herein) to produce a final wellbore fluid having an acceptable level of a microbial population.

DETAILED DESCRIPTION

Modifications to embodiments described in this document, and other embodiments, will be evident to those of ordinary skill in the art based on the information provided herein. In case of conflict, the specification of this document, including definitions, will control.

Each example is provided by way of explanation of the present disclosure and is not a limitation thereon. In fact, it will be apparent to those skilled in the art that various modifications and variations can be made to the teachings of the present disclosure without departing from the scope of the disclosure as defined by the attached claims.

References to singular characteristics or limitations of the present disclosure include the corresponding plural characteristic(s) or limitation(s) and vice versa, unless otherwise specified or clearly implied to the contrary by the context in which the reference is made.

The present proposals are based on a method comprising measuring one or more microbial parameters of a system and using this measurement to select or optimize a microbial control treatment. The proposals may further comprise monitoring of the microbial parameter over a given time period or taking two or more distinct, temporally separated, measurements of the microbial parameter, and adjusting or selecting the microbial control treatment based on the behavior of the microbial parameter over time.

In one aspect the present proposals describe an integrated system of first measuring the bacteria and water chemistry in a fracking water source (i.e., water that has not yet been injected into a wellbore) to determine the amount of bacteria present. Using this information a chemical treatment can be proposed that is proportionate to the amount of bacteria present. There are different modes of action and expected outcomes of water treated with oil and gas bacteria control agents. Some chemicals are known to kill bacteria and other agents prevent reproduction of bacteria. The present methods seek to standardize treatment based on the outcome of bacteria and chemical testing. Knowing the water chemistry, fracturing fluid formulation, formation temperature and the amount of bacteria present will allow selection from many different chemical and physical methods for controlling bacteria to a level that will not present a risk to the asset (e.g. wellbore). Also proposed herein are methods including testing of the proppant used in the fracturing process to see if it contains problematic levels of bacteria. If bacteria are found to be present, chemical control agents may be introduced that can control the bacteria that will be released into the fracturing fluid from the proppant down hole.

Figure 1:
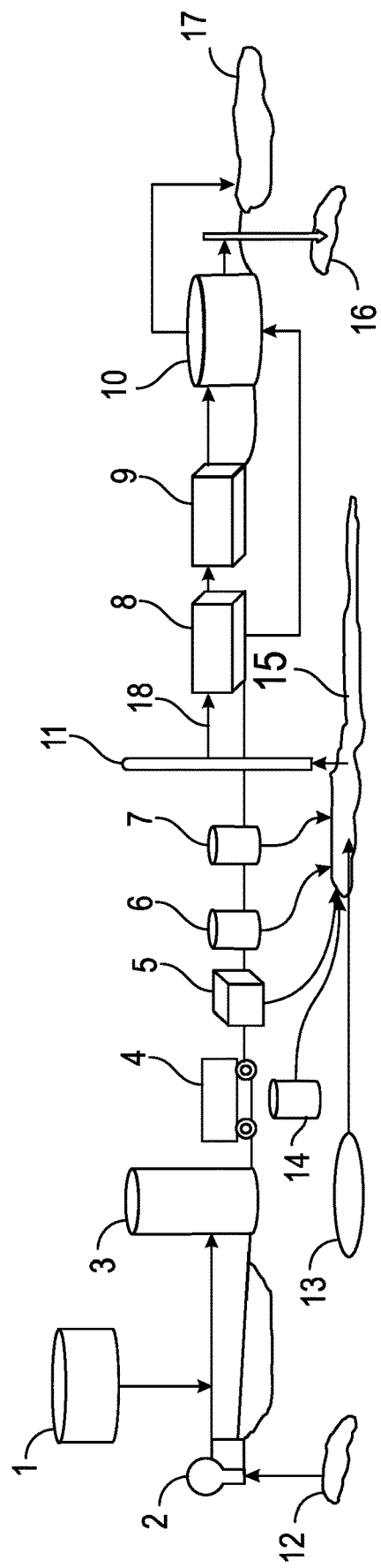
FIG. 1 depicts various sites in an oilfield operation at which the methods described herein may be applicable.
Figure 2:
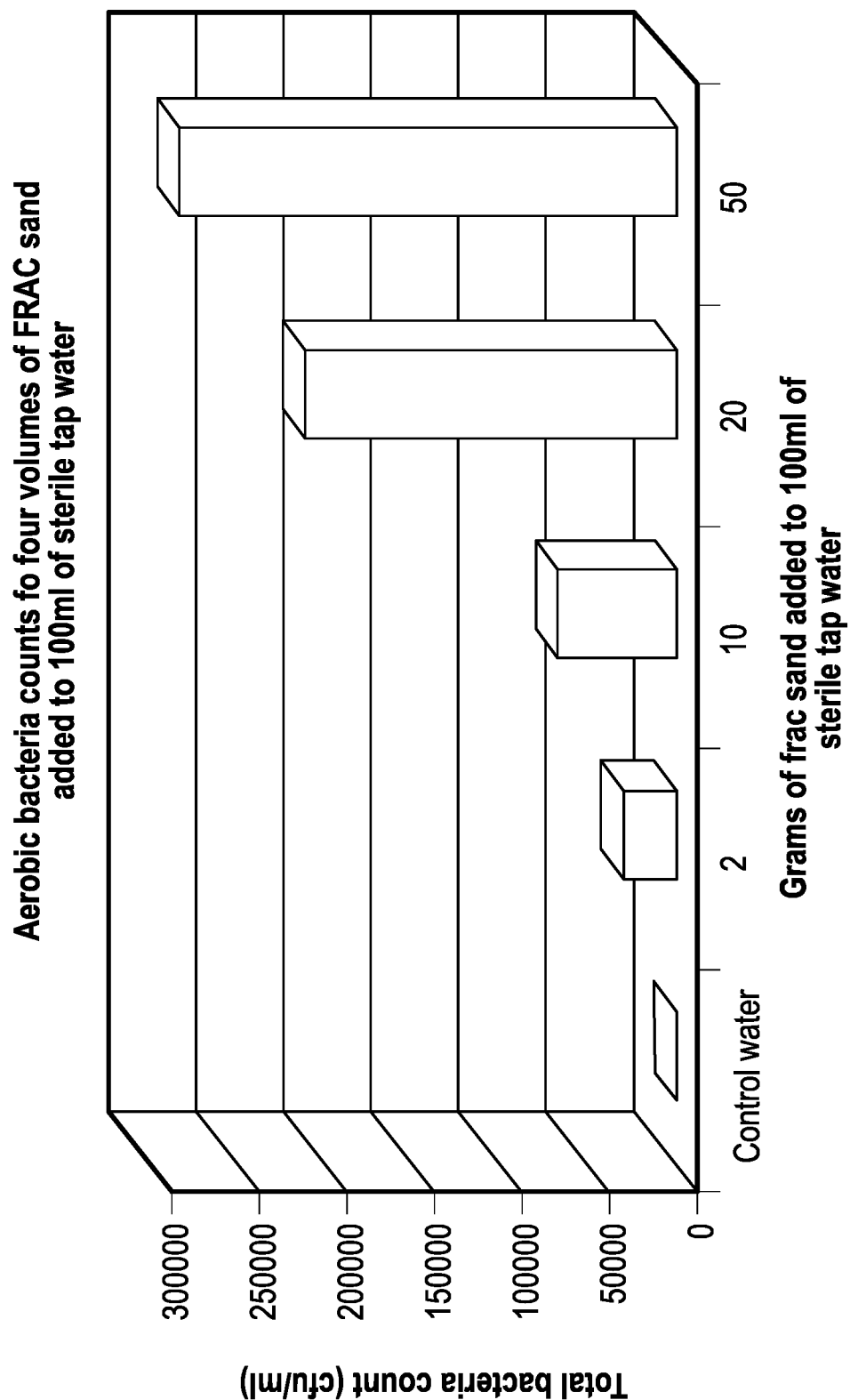
FIG. 2 illustrated real-time monitoring of a bacterial parameter and various possible sites at a fracturing location where these methods are applicable.

The steps of the present methods may be performed at any point in the oilfield production, refining, transporting, and storage process. FIG. 1 illustrates examples of suitable points in this process at which one or more steps of the present methods may be performed, for example, a water tank 1, water well 2, water storage vessel 3, water tanker 4, drilling muds 5, drilling fluids 6, frac fluids 7, pressure wash 8, solids separation 9, waste liquids 10, fresh or brine aquifer 12, well and product 11, water-flooding 13, treatment liquids 14, reservoir 15, deep well disposal 16, or disposal pond 17

Measuring

The present methods include a step of measuring a microbial parameter of a given system. The microbial parameter may comprise one or more of: total amount of microbes present, e.g. microbial concentration; type of microbes present, e.g. identification of the presence of a specific microbe, or more general identification of the presence of a given class of microbe; ratio of different types of microbes, e.g. amount of one type of microbe relative to another. In some aspects the microbial parameter corresponds to the concentration of a given type of microbe in the system, e.g. concentration of bacteria in a given volume of fluid.

In one aspect, the step of measuring a microbial parameter may include use of a measuring device that targets a naturally occurring enzyme activity in bacteria that is present in a broad spectrum of bacteria representing most major taxonomic groups, including gram negative and gram positive bacteria, as well as aerobes and anaerobes. This enzyme activity may belong to a class of enzymes called hydrolases. In these aspects, the measurement device is very sensitive to the presence of bacteria in water samples including suspended as well as bacteria immobilized on particles or in aggregates. In addition, using such a measurement device, bacterial contaminants can be concentrated from large volumes of water allowing low analysis time even at relatively low bacterial concentrations.

In the present proposals, microbes may include any bacteria, archaea, protozoa, algae, or fungus. In particular aspects the microbes are bacteria. In particular aspects, the microbes are bacteria expressing a hydrolase enzyme.

Examples of bacteria that express the target hydrolase enzyme activity are provided in Table 1 below. The bacteria may include gram positive, or gram negative bacteria. The bacteria expressing the hydrolase enzyme include representatives from most major taxonomic groups.

TABLE 1

| Organism | Gram stain | Phylum/class |
|---|---|---|
| Athrobacter sp. | Negative | Actinobacteria/grp. 20 |
| Bacillus cereus | Positive | Firmicutes/grp. 18 |
| Bacillus subtilis | Positive | Firmicutes/grp. 18 |
| Bacillus thuringiensis | Positive | Firmicutes/grp. 18 |
| Clostridiumtetani | Positive | Firmicutes/clostridia |
| Desulfovibrio desulfouricans | Positive | Proteobacteria/δ |
| Enterobacter sp. | Negative | Proteobacteria/γ |
| Enterococcous faecalis | Positive | Firmicutes/bacilli |
| Eschericia coli | Negative | Proteobacteria/γ |
| Escherichia fergusonii | Negative | Proteobacteria/γ |
| Flavobacteriabacterium | Negative | Bacteroidetes/flavobacteria |
| Flavobacterium johnsoniae | Negative | Bacteroidetes/flavobacteria |
| Klebsiella pneumonia | Negative | Proteobacteria/γ |
| Lactobacillus acidophilus | Positive | Firmicutes/bacilli |
| Lactobacillus reuteri | Positive | Firmicutes/bacilli |
| Methanococcus aeolicus | Negative | Euryarchaeota/methanococci |
| Micrococcus sodonensis | Positive | Actinobacteria/actinobacteria |
| Pseudomonas aeroginosa | Negative | Proteobacteria/γ |

TABLE 1-continued

| Organism | Gram stain | Phylum/class |
|---|---|---|
| Rhodobacter sphaeroides | Negative | Proteobacteria/α |
| Serratia marcescens | Positive | Proteobacteria/γ |
| Staphylococcous aureus | Positive | Firmicutes/bacilli |
| Sphingomonas Wittichii | Negative | Proteobacteria/α |
| Vibrio sp. | Negative | Proteobacteria/γ |
| Xanthomonas campestris | Positive | Proteobacteria/γ |

When considering methods for measuring concentrations of microbes in a sample, traditional plate counts are time consuming and cumbersome to perform. Furthermore, they provide limited information that is useful for making decisions about water treatment processes because the plate counts includes less than 1% of the bacteria present in a water sample. Furthermore, and relevant to the present proposals, traditional plate counts do not include quantification of particle associated bacteria, e.g. bacteria associated with solid materials such as a proppant component.

The present proposals use a device for measurement which provides a rapid method for quantification of total bacteria, reducing analysis time from days to hours or minutes. This speed of measurement is an advantage of the present methods. Known methods of bacterial measurement such as plate growth methods take many days or weeks to provide a result. For example analysis by growth of a bacterial sample on a plate and assessment (e.g. counting) of the resulting culture may take at least 48 hours; analysis by growth of a sample using serum bottles may take anywhere from 7 to 28 days; analysis by polymerase chain reaction (PCR) might take days to weeks to return results. By contrast, the present methods can give a result on a timescale of hours or even minutes, e.g. within about 24 hours, or within about 12 hours, or within about 6 hours, or within about 2 hours, or within about 60 minutes, or within about 30 minutes, or within about 15 minutes, or within about 10 minutes, or within about 5 minutes. In many cases the results are not provided in less than about 5 minutes, and in some cases not less than about 15 minutes.

The measurement device may be embodied in portable equipment for on-location use, stationary equipment for lab based operations, tailored solutions to specific requirements, or special packaging solutions for use under rugged conditions. Furthermore, the measurement device may be configured to work with specialized data handling software for analyzing and reporting results.

The measurement device functions by reacting an aqueous sample with a filter unit that has been saturated with a surplus of enzyme substrate. The enzyme substrate reacts with a naturally occurring bacterial enzyme and a fluorescent compound is released which can then be detected. The reaction time may be approximately 15-30 minutes depending on the application and particular process parameters. The amount of fluorescence is measured using a handheld battery operated fluorometer. The level of fluorescence can be directly related to the amount of bacteria present in the sample so a bacterial concentration can be calculated. The more fluorescence produced the more bacteria is present in the sample. Typical recommended sampling volumes range from 10-1000 ml depending on the application.

A typical measuring device is described in PCT publication WO 2014/085333, the entire disclosure of which is incorporated herein by this reference.

The present methods are applicable to any aqueous fluid used in, or for use in, an oilfield operation or a pre- or post-production process associated with wellbore production. For example, the aqueous fluid may be selected from the group consisting of: any aqueous wellbore stimulation fluid, e.g. a fracturing fluid; a completion fluid; a wellbore fluid for circulation during or after drilling operations; an aqueous fluid used in workover operations; aqueous fluids used in treatment of any oilfield or refinery component, e.g. pipe, line, manifold, production tree, or other conduit, tank or storage vessel, or transport container; an aqueous fluid used during a refining process; and water or other aqueous fluid stored at an oilfield location, e.g. in a reservoir or pond, for use in oilfield processes (such as injection into a wellbore).

In some aspects, the aqueous fluid is a fracturing fluid or a wellbore fluid for circulation during or after drilling operations, for example a fracturing fluid.

The aqueous fluid may further comprise typical oilfield fluid components including but not limited to one or more of hydrocarbons, surfactants, emulsifiers, corrosion inhibitors, scaling agents, friction reducers, crosslinkers, weighting agents, or proppants.

In some aspects the methods relate to control of a microbial level on a solid component for use in an aqueous fluid used in, or for use in, an oilfield operation or a pre- or post-production process associated with wellbore production. The solid component may be selected from the group consisting of proppants, weighting agents, or any other solid (e.g. particulate) component suitable for addition to an aqueous fluid used in, or for use in, an oilfield operation or a pre- or post-production process associated with wellbore production. In some aspects, the solid component is a proppant component for use in an aqueous fracturing fluid.

In the methods described herein, the measuring step may take place at any suitable time before, during, or after use of the aqueous fluid or solid component in an oilfield or a pre- or post-production process associated with wellbore production.

In some aspects, the measuring step is performed before the use of the aqueous fluid or solid component. These aspects may include conducting the measuring step on a new, unused aqueous fluid or solid component, or may include conducting the measuring step on a recycled fluid or solid component, e.g. a fluid that has been filtered or otherwise treated following use so as to recycle it for repeated use, such as a recycled or filtered wellbore fluid.

In some aspects, the measuring step is performed during use. This may include extracting a sample from a fluid flow or a fluid reservoir and conducting the measuring step on the extracted sample. For example, in these aspects, the measuring step may be performed when a wellbore fluid is returned to the surface and prior to reinjection into the formation.

In some aspects, the measuring step is performed after use of the aqueous fluid or solid component, e.g. fluid or solid component to be recycled or disposed of as waste.

The measuring step may be performed on-site, e.g. at an oilfield or wellbore location, a refinery, a transport location for transporting oilfield materials or products, a storage facility, or a supplier of raw materials for use in the oilfield industry. Alternatively or additionally the measuring step may be performed off-site, e.g. a sample of the aqueous fluid or solid component may be removed and the measuring step conducted at a separate test facility.

The result of the measuring step may be reported in units that are standard in the oilfield industry. For example "log" values which may represent the outcome of a known test for bacterial levels are well understood in the industry, so the present methods may present the measurement results in these units. Therefore the methods may include a step of converting the measured microbial parameter (e.g. the concentration of microbes present in a sample) into industry standard units, such a "log" values.

Bacterial Control

In the methods described herein, the results of the measuring step are used to inform a decision about a suitable microbial control treatment. As used herein, the term "control" is defined to include both inhibition of growth or replication, and removal. Therefore, microbial control includes inhibition of microbial growth or replication, reduction in the concentration of microbes in a sample, treatment of the sample to render the environment hostile to microbes, and killing microbes in the sample to either completely or partially remove them from the sample.

The outcome of the measuring step in the present methods is used to influence the decision about a suitable microbial control treatment. Any of the relevant microbial parameters mentioned above in relation to the measuring step may be used to influence this decision. The overall level (e.g. concentration or total amount) of microbes in the sample may be used to influence the decision about a suitable microbial control treatment.

Figure 5:
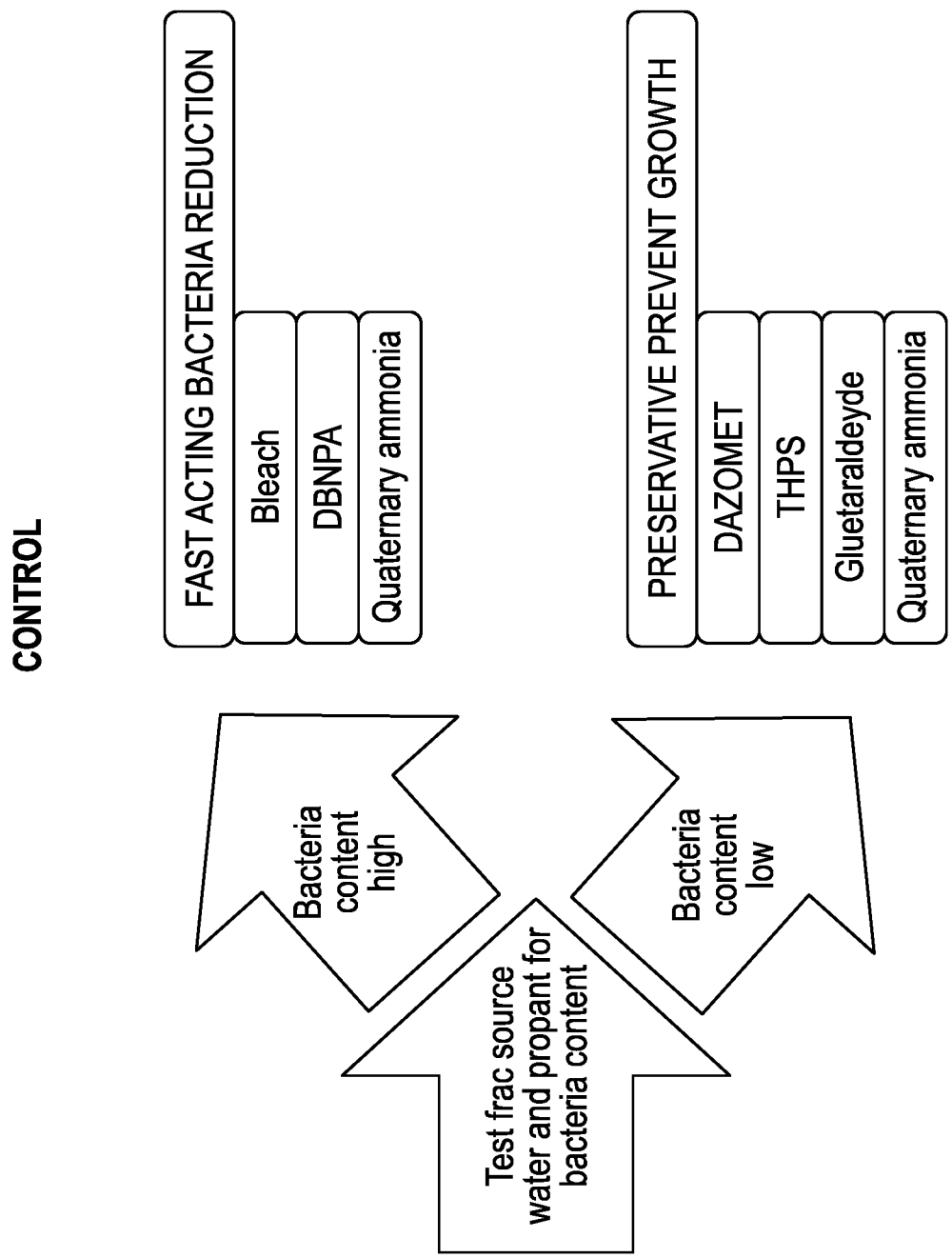
FIG. 5 shows a decision tree for selecting an appropriate antimicrobial treatment based on the outcome of measurement of microbial concentration in an aqueous sample.

In one aspect, the microbial control treatment is selected according to the concentration of microbes in the sample as set out in FIG. 5. In this aspect, samples having a high microbial concentration, e.g. above about 10000 colony forming units (cfu) per ml, or possibly above about 5000 cfu/ml may be advantageously treated with a fast-acting microbial control treatment (e.g. selected from bleach, 2,2-dibromo-3-nitrilopropionamide (DBNPA), or quaternary ammonium salt). In a similar way, samples having a low microbial concentration, e.g. below about 1000 colony forming units (cfu) per ml may be advantageously treated with a preventative or slower acting microbial control treatment (e.g. selected from 3,5-Dimethyl-1,3,5-thiadiazinane-2-thione (DMTT), tetra-kis-hydroxymethyly-phosphonium sulfate (THPS), or certain quaternary ammonium salts.

Additional factors may also be taken into account in making the decision about a suitable microbial treatment. For example, these additional factors may include one or more factors selected from the group consisting of water chemistry, the nature of the aqueous fluid, formation temperature, propant microbial (e.g. bacterial) load, contact time, local groundwater composition (e.g. pesticide concentration). In terms of the nature of the aqueous fluid, this may include one or more of, pH, viscosity, composition (e.g. the presence of any components that are incompatible with certain microbial control treatments), and salinity.

Accordingly the present methods may include a step of using one or more additional factors (in addition to the microbial parameter measured in the measuring step) to influence the decision about a suitable microbial treatment. In some embodiments, the one or more additional factors are selected from water chemistry, the nature of the aqueous fluid (e.g. fracturing fluid), formation temperature, propant microbial (e.g. bacterial) load.

Suitable microbial treatments may be selected from addition of any biocide or antimicrobial agent. Typical microbial treatments are available in the art and their selection is influenced, in the present methods, as explained herein.

In some aspects, the microbial treatment is tailored to the specific parameters of the system being treated. For example some antimicrobial agents are effective following treatment over a long timescale. For samples or fluids that are present in a system for a short time period, such a treatment would not be suitable.

As explained herein in relation to the measuring step, in the methods described herein, the application of a microbial control treatment may take place at any suitable time before, during, or after use of the aqueous fluid or solid component in an oilfield or a pre- or post-production process associated with wellbore production, providing the control treatment takes place after the measuring step.

In some aspects, the microbial control treatment is performed before the use of the aqueous fluid or solid component. These aspects may include conducting the microbial control treatment on a new, unused aqueous fluid or solid component, or may include conducting the microbial control treatment on a recycled fluid or solid component, e.g. a fluid that has been filtered or otherwise treated following use so as to recycle it for repeated use, such as a recycled or filtered wellbore fluid.

In some aspects, the microbial control treatment is performed during use. This may include extracting a sample from a fluid flow or a fluid reservoir and conducting the microbial control treatment on the extracted sample. For example, in these aspects, the microbial control treatment may be performed when a wellbore fluid is returned to the surface and prior to reinjection into the formation.

In some aspects, the microbial control treatment is performed after use of the aqueous fluid or solid component, e.g. a fluid or solid component to be recycled or disposed of as waste.

The microbial control treatment may be performed on-site, e.g. at an oilfield or wellbore location, a refinery, a transport location for transporting oilfield materials or products, a storage facility, or a supplier of raw materials for use in the oilfield industry. Alternatively or additionally the microbial control treatment may be performed off-site, e.g. a sample of the aqueous fluid or solid component may be removed and the microbial control treatment conducted at a separate facility.

A suitable microbial treatment (e.g. using chemical agents) is selected based on the specific demands of present by the integration of factors as disclosed herein and including the microbial parameter measured in the measuring step of the methods as defined herein. In some aspects, selection of the chemical agents may be based on the Environmental Protection Agency (EPA), mode of action and physical limitations necessitating integration of the aforementioned factors.

A suitable microbial control treatment may be selected from the group consisting of chemical treatment agents, ultra violet radiation (UV), ultra-filtration, thermal treatment, ionizing radiation, non-ionizing radiation, and other treatment processes known to a skilled person to be effective to control a microbial population.

In some aspects, the microbial treatment is a chemical agent. In such aspects, the chemical agent may be selected from biocides, antimicrobial agents, and oxygen scavengers.

In some aspects the chemical treatment agent may be selected from glutaraldehyde, tetra-kis-hydroxymethyly-phosphonium sulfate (THPS), quaternary ammonium salts, a gluteraldehyde combination with quaternary ammonium salt(s), 2,2-dibromo-3-nitrilopropionamide (DBNPA), bronopol, Dazomet, methyl isothiocyanate, Tributyltetradecyl-phosphonium Chloride (TTPC), Alkyl Dimethyl Benzyl Ammonium Chloride (ADBAC), Dicecyldimethylammoniumchloride (DDAC), sodium hypochlorite, chlorine dioxide, hydrogen peroxide, ozone, bromous acid, and perchloric acid. In some aspects the chemical treatment agent may be selected from the group consisting of glutaraldehyde or tetra-kis-hydroxymethyly-phosphonium sulfate (THPS). In some aspects the chemical treatment agent may be selected from the group consisting of quaternary ammonium salts, sodium hypochlorite, chlorine dioxide, hydrogen peroxide, ozone, bromous acid, and perchloric acid.

Under certain circumstances, the microbial treatment is selected to have minimal or no interaction with the components of the aqueous fluid or solid component being treated. For example, the microbial treatment should not affect fluid viscosity or performance of oxygen scavengers.

Further desirable properties for the microbial treatment include: cost effectiveness (e.g. low cost per liter, low cost per unit volume or area treated); safety (e.g. low personnel risk, minimal neutralization requirements, low environmental impact; compatibility with other wellbore fluids (e.g. solubility, partition coefficient, pH, absence of $H_2S$ production, hardness, compatibility with metal ions or sulfates in solution); and ease of handling (e.g. low corrosiveness, especially towards metals and elastomers, low freezing point, and thermal stability).

In some aspects, the antimicrobial treatment is chlorine dioxide.

Antimicrobial treatment may be continued or repeated until the microbial population is at an acceptable level. The term "acceptable" in this context refers to any amount of microbes that one of ordinary skill in the art would deem as not being detrimental to the oilfield operations.

Monitoring

After testing and treatment of the aqueous fluid (e.g. fracturing water) ongoing testing may be performed to ensure that the chemical agents used have been effective in controlling the microbes (e.g. bacteria in the water and the proppant).

The present methods may therefore further include a step of monitoring of a microbial parameter in the aqueous fluid or on the solid component over a time period or at a second point in time after the initial measurement. This monitoring over time or at a later time point allows the effectiveness of the microbial control to be evaluated. Furthermore, the monitoring step may determine that the microbial parameter is outside a desired threshold limit which may suggest an additional microbial control step to be performed.

This monitoring over a time period or at a second point in time after the initial measurement may take place over any time period suitable for the specific system being monitored. For example if the system is rapidly evolving, more frequent monitoring may be requisite than for a more static system.

The present method may further comprise adjusting or repeating the antimicrobial treatment according to changes in the microbial parameter over time.

In some aspects, the monitoring step may comprise monitoring a microbial parameter at regular time intervals, or continuously, and adjusting a microbial control accordingly to maintain the microbial parameter within a desired range.

EXAMPLES

The present proposals are further illustrated by the following specific examples. These examples are provided to illustrate the proposals and do not unnecessarily limit them.

In a standard test well, after the well is put into production we propose a system to test for bacteria, not only and the well head, but in the entire production string. We have found that downhole temperatures are often too high to support the growth of damaging bacteria. Often bacteria can become established, grow and reproduce in surface fluid processing equipment when the fluid coming from the well remains bacteria free. We propose a system to collect in-process samples from production equipment to ensure the bacteria have not become established. Further if bacteria are found we can introduce chemical control agents that will remove the bacteria and then keep them under control.

We will also conduct testing during a fracturing operation to ensure that the chemical agents are being added at the correct concentration and directly test the bacteria with methods described herein that produce results in 20 minutes. The monitoring allows for adjustment of the chemical feeds to ensure proper treatment is being achieved. The monitoring extents to the pond used as fracturing water.

Example 1

A sample of frac sand was secured from an active frac site in Texas.

Figure 3:
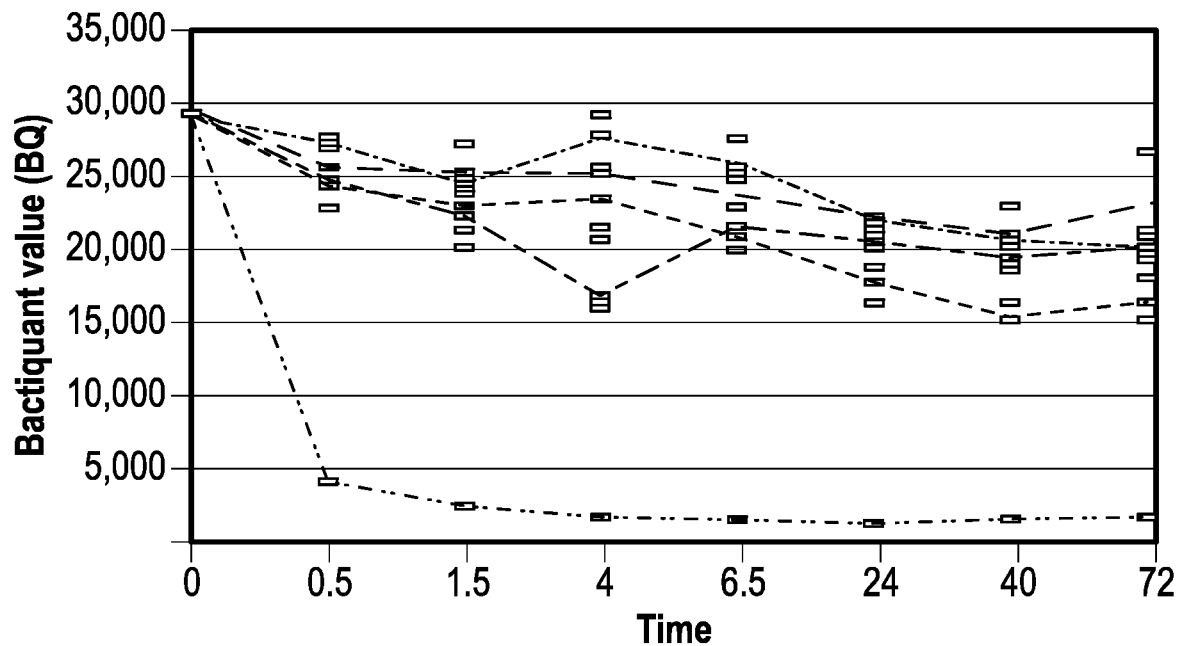
FIG. 3 shows a graph obtained by adding different amounts of fracturing sand to sterile tap water and then measuring the concentrations of bacteria in the aqueous fluid as set out in Example 1.

2, 10, 20 and 50 grams of sand was added to frac source water that had been sterilized in an autoclave. The water was held in contact with the sand for 8 hrs. The bacteria content of the water was determined with standard heterotrophic plate count. Results are presented in FIG. 3.

Example 2

Figure 4:
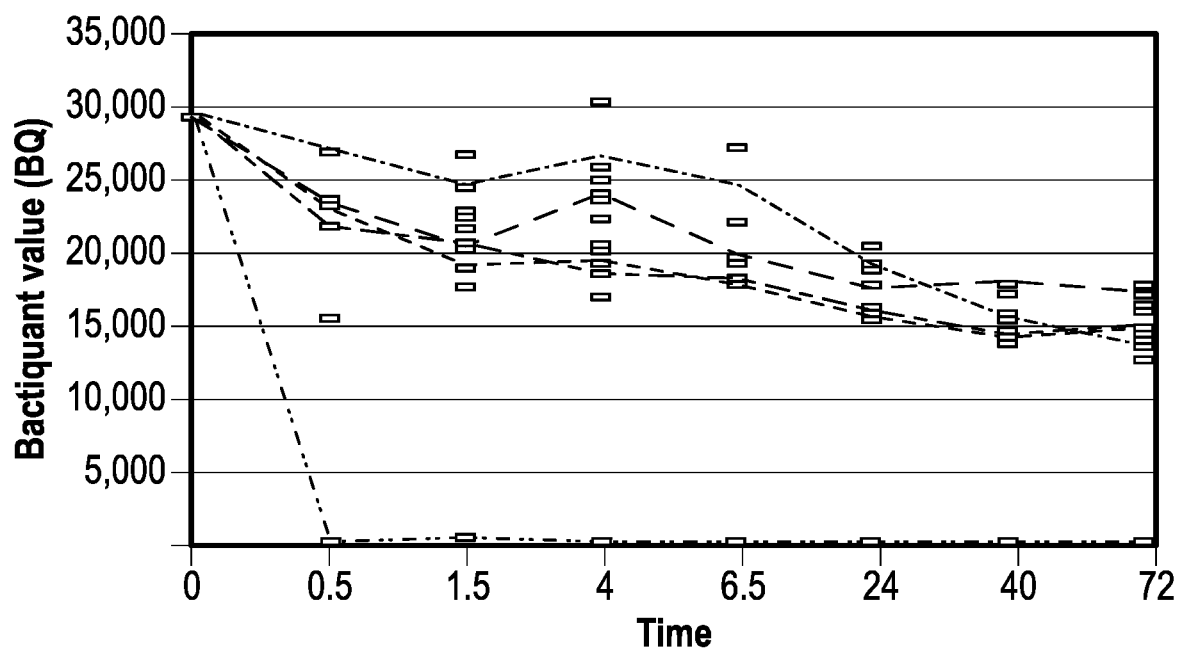
FIG. 4 shows monitoring of bacterial levels at different points during a 72 hour period following addition of a range of different antibacterial agents; as set out in Example 2.

A 5 gallon sample of frac source water was secured from an active frac operation in South Dakota. The sample was mixed and split into multiple 1 liter samples. The samples were treated with five different biocides at the lowest labeled and the highest label rate. The bacteria content of the water was measured in triplicate after 0.5, 1.5, 4, 6.5, 24, 48, and 72 hours using a measuring device. One sample was untreated as a control and measured at the same time intervals. Results are shown in FIG. 4.

Example 3

Figure 6:
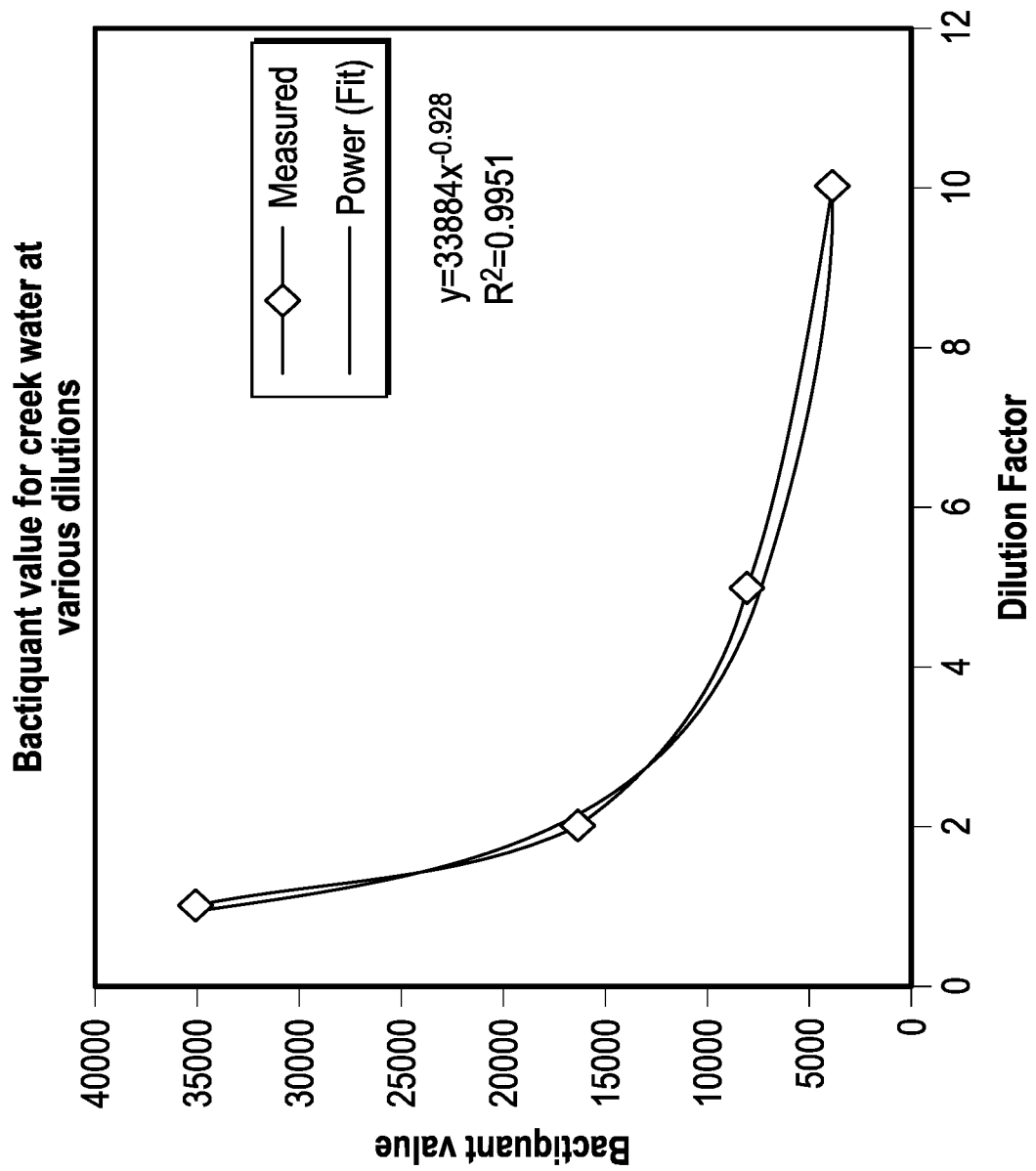
FIG. 6 shows bacterial levels in frac water samples diluted to varying levels with sterilized frac water; as set out in Example 3.
Figure 7:
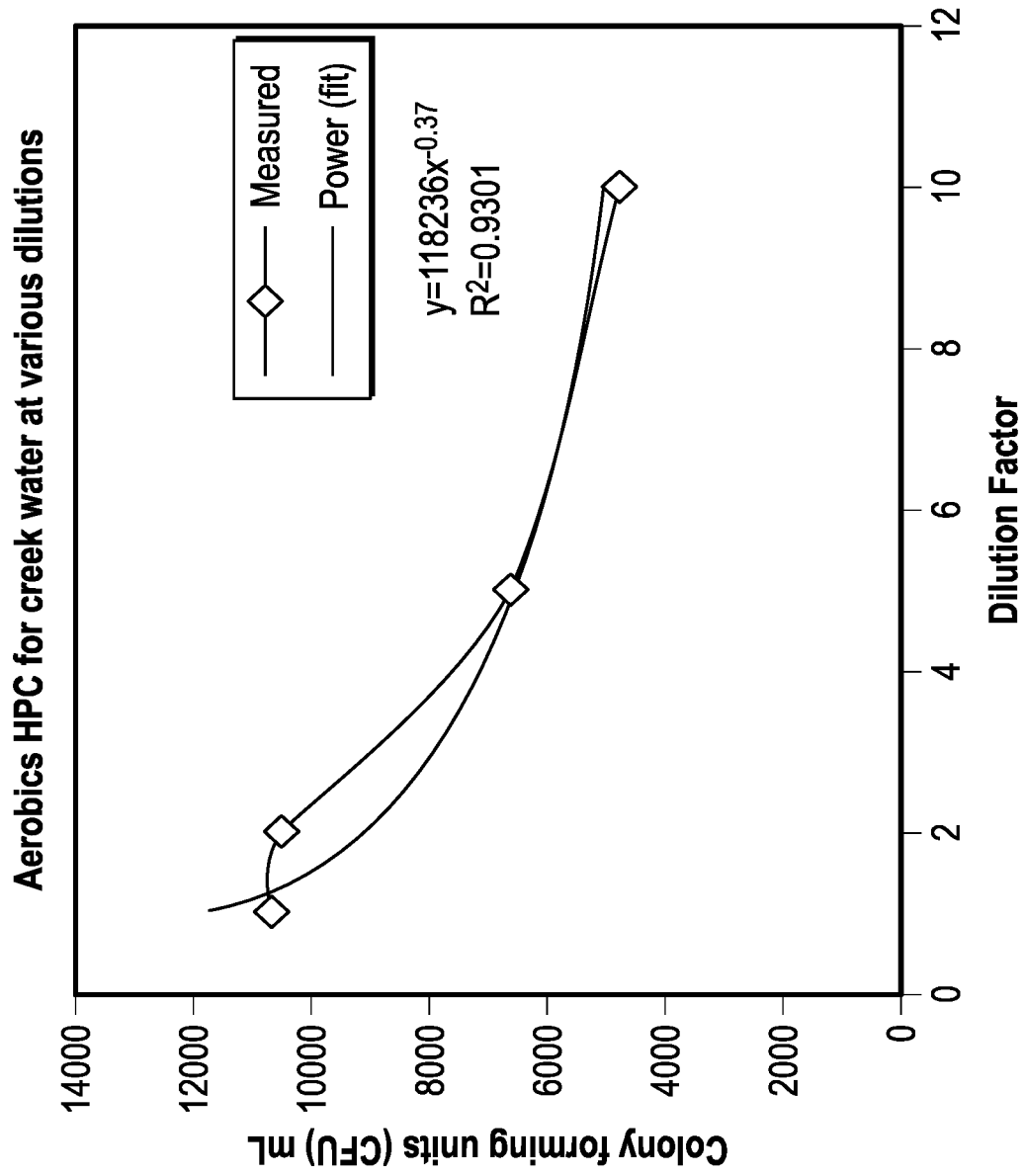
FIG. 7 shows bacterial levels determined by standard heterotrophic plate count in frac water samples diluted to varying levels with sterilized frac water; as set out in Example 3.

Description of FIGS. 6 & 7
A sample of raw water used as a frac source was obtained. A portion of the water was sterilized in an autoclave. The raw, non-autoclaved, water was diluted at three different dilution levels with the autoclaved water to produce four test samples (one raw water sample and three diluted ones). Each of the four samples were split into two portions. The bacteria content of the first portion was determined using a measuring device and the results are shown in FIG. 6. The bacteria content of the second portion was determined using standard heterotrophic plate count and the results are presented in FIG. 7. This allows for comparisons of the two measurement methods and it can be seen that they are comparable.

It will be understood that various details of the presently disclosed subject matter can be changed as understood by a skilled reader without departing from the scope of the proposals as defined by the present claims.

What is claimed is:
1. A method of controlling a microbial level in an aqueous fluid used in an oilfield operation or a pre- or post-production process associated with wellbore production, the method comprising:
measuring a microbial parameter of the aqueous fluid;
determining an appropriate antimicrobial treatment based on the measured microbial parameter and one or more factors selected from the group consisting of water chemistry, nature of the aqueous fluid, formation temperature and proppant microbial load, and
performing the appropriate antimicrobial treatment,
wherein the appropriate microbial treatment consists of at least one chemical treatment agent selected from the group consisting of glutaraldehyde, tetra-kis-hydroxymethyly-phosphonium sulfate (THPS), quaternary ammonium salts, a gluteraldehyde combination with quaternary ammonium salt(s), bronopol, Dazomet, methyl isothiocyanate, Tributyltetradecylphosphonium Chloride (TTPC), Alkyl Dimethyl Benzyl Ammonium Chloride (ADBAC), Dicecyldimethylammoniumchloride (DDAC), chlorine dioxide, ozone, bromous acid, and perchloric acid.

2. The method of claim 1, further comprising:
monitoring the microbial parameter in the aqueous fluid over a time period or at a second point in time after an the initial measurement.

3. The method of claim 2, further comprising:
adjusting the appropriate antimicrobial treatment according to changes in the microbial parameter over time.

4. The method of claim 1, wherein the microbial parameter of the aqueous fluid comprises at least one of:
a concentration of microbes;
a type of microbes; and
a ratio of different types of microbes.

5. The method of claim 1, wherein the aqueous fluid is selected from the group consisting of a drilling fluid, a completion fluid, and a fracturing fluid.

6. The method of claim 1, wherein the at least one chemical treatment agent is selected from the group consisting of glutaraldehyde, tetra-kis-hydroxymethyly-phosphonium sulfate (THPS), quaternary ammonium salts, a gluteraldehyde combination with quaternary ammonium salt(s), bronopol, Dazomet, Tributyltetradecylphosphonium Chloride (TTPC), chlorine dioxide, ozone, bromous acid, and perchloric acid.

7. A method of controlling a microbial level on a solid component for use in an aqueous fluid used in an oilfield operation or a pre- or post-production process associated with wellbore production, the method comprising:
measuring a microbial parameter of the solid component;
using the measured microbial parameter to decide on an appropriate antimicrobial treatment and one or more factors selected from the group consisting of water chemistry, nature of the aqueous fluid, formation temperature and proppant microbial load, and
performing the appropriate antimicrobial treatment
wherein the appropriate microbial treatment consists of at least one chemical treatment agent selected from the group consisting of glutaraldehyde, tetra-kis-hydroxymethyly-phosphonium sulfate (THPS), quaternary ammonium salts, a gluteraldehyde combination with quaternary ammonium salt(s), bronopol, Dazomet, methyl isothiocyanate, Tributyltetradecylphosphonium Chloride (TTPC), Alkyl Dimethyl Benzyl Ammonium Chloride (ADBAC), Dicecyldimethylammoniumchloride (DDAC), chlorine dioxide, ozone, bromous acid, and perchloric acid.

8. The method of claim 7, wherein the appropriate antimicrobial treatment is performed on the solid component prior to addition to the aqueous fluid.

9. The method of claim 7, wherein the appropriate antimicrobial treatment is performed on the aqueous fluid following addition of the solid component.

10. The method of claim 7, wherein the appropriate antimicrobial treatment is performed both prior to and following addition of the solid component to the aqueous fluid.

11. The method of claim 7, further comprising:
monitoring the microbial parameter of the solid component over a time period or at a second point in time after an the initial measurement.

12. The method of claim 11, further comprising:
adjusting the appropriate antimicrobial treatment according to changes in the microbial parameter over time.

13. The method of claim 7, wherein the microbial parameter of the solid component comprises at least one of:
a concentration of microbes;
a type of microbes; and
a ratio of different types of microbes.

14. The method of claim 7, wherein the aqueous fluid is selected from the group consisting of a drilling fluid, a completion fluid, and a fracturing fluid.

15. The method of claim 7, wherein the chemical agent is selected from the group consisting of glutaraldehyde, tetrakis-hydroxymethyly-phosphonium sulfate (THPS), quaternary ammonium salts, a gluteraldehyde combination with quaternary ammonium salt(s), bronopol, Dazomet, Tributyltetradecylphosphonium Chloride (TTPC), chlorine dioxide, ozone, bromous acid, and perchloric acid.

\* \* \* \* \*